United States Patent
Johnstone et al.

(10) Patent No.: US 8,865,719 B2
(45) Date of Patent: Oct. 21, 2014

(54) SUBSTITUTED HETEROCYCLES AND THEIR USE AS ALLOSTERIC MODULATORS OF NICOTINIC AND GABA$_A$ RECEPTORS

(75) Inventors: Timothy B. C. Johnstone, Costa Mesa, CA (US); Derk J. Hogenkamp, Carlsbad, CA (US); Kelvin W. Gee, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/255,781

(22) PCT Filed: Mar. 9, 2010

(86) PCT No.: PCT/US2010/026645
§ 371 (c)(1),
(2), (4) Date: Dec. 13, 2011

(87) PCT Pub. No.: WO2010/104843
PCT Pub. Date: Sep. 16, 2010

(65) Prior Publication Data
US 2012/0077816 A1   Mar. 29, 2012

Related U.S. Application Data

(60) Provisional application No. 61/158,684, filed on Mar. 9, 2009.

(51) Int. Cl.
*A61K 31/50* (2006.01)
*A61K 31/501* (2006.01)
*C07D 487/00* (2006.01)

(52) U.S. Cl.
USPC ............... 514/252.06; 544/235; 544/236

(58) Field of Classification Search
USPC ............ 544/235, 236; 514/252.05, 252.06
See application file for complete search history.

(56) References Cited

U.S. PATENT DOCUMENTS

2009/0098181 A1   4/2009   Lu et al.

FOREIGN PATENT DOCUMENTS

| WO | WO2007064797 | 6/2007 |
|----|--------------|--------|
| WO | WO2007075567 | 7/2007 |
| WO | WO2008008539 | 1/2008 |
| WO | WO2008051805 | 5/2008 |

OTHER PUBLICATIONS

Vippagunta et al. (2000).*
Wolff et al (1995).*
Banker et al. (1996).*
International Preliminary Report on Patentability for PCT/2010/026645, mailed Sep. 12, 29011, 6 pages.
International Search Report for PCT/2010/026645, mailed Oct. 26, 2010, 5 pages.
Written Opinion for PCT/2010/026645, mailed Oct. 26, 2010, 5 pages.

* cited by examiner

*Primary Examiner* — Paul V. Ward
(74) *Attorney, Agent, or Firm* — Richard H. Pagliery; TechLaw LLP

(57) ABSTRACT

The present invention is related to heterocycles represented by a compound of Formula I that are novel allosteric modulators of α7 nAChRs and/or GABA$_A$ receptors. The invention also discloses the treatment of disorders that are responsive to enhancement of acetylcholine action on α7 nAChRs and negative allosteric modulation of GABA$_A$ receptors in a mammal by administering an effective amount of a compound of Formula I.

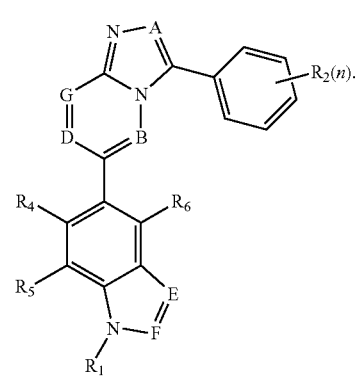

5 Claims, No Drawings

SUBSTITUTED HETEROCYCLES AND THEIR USE AS ALLOSTERIC MODULATORS OF NICOTINIC AND GABA$_A$ RECEPTORS

RELATED APPLICATIONS

This application is a national stage application of International Application No. PCT/US2010/026645 which claims the benefit of U.S. Provisional Application No. 61/158,684, filed Mar. 9, 2009, which is herein incorporated by reference in its entirety.

FIELD OF THE INVENTION

This invention is in the field of medicinal chemistry. In particular, the invention relates to substituted heterocycles and their derivatives and the discovery that these compounds allosterically modulate the nicotinic acetylcholine receptor (nAChR) and GABA$_A$ receptors in a therapeutically relevant fashion and may be used to ameliorate CNS disorders amenable to modulation of the nAChR and GABA$_A$ receptors.

BACKGROUND OF THE INVENTION

α7 nAChRs belong to the ligand-gated ion channel superfamily of Cys-loop receptors. The Cys-loop superfamily includes muscle and neuronal nAChRs, 5-hydroxytryptamine type 3 (5HT$_3$), γ-aminobutyric acid$_A$ (GABA$_A$), GABA$_C$ and glycine receptors. α7 nAChRs are allosteric proteins which recognize acetylcholine and choline as the orthosteric ligand and bind nicotine at the orthosteric site. Neuronal α7 nAChRs contain 5 orthosteric sites per receptor. Agonist binding to the orthosteric site transmits an allosteric effect which modulates the functional states of the receptor depending on the concentration and kinetics of agonist application. Four functional states have been described for nAChRs: one open and three closed states (resting, fast-onset desensitized, slow-onset desensitized). Activation of neuronal nAChRs mediates fast synaptic transmission and controls synaptic transmission by the major inhibitory and excitatory neurotransmitters, GABA and glutamate.

α7 nAChRs mediate the predominant nicotinic current in hippocampal neurons. The α7 nAChR was initially identified from a chick brain library as an α-bungarotoxin binding protein that exhibits ~40% sequence homology to other nAChRs. α7 nAChRs share similar features of other neuronal and muscle nAChRs such as a pentameric Cys-loop receptor structure and M2 segment of each subunit lining of the channel pore, however the α7 nAChR exhibits a homopentameric structure when reconstituted in *Xenopus oocytes*, a characteristic shared only with the α8 and α9 nAChRs. Heterologously expressed homomeric α7 nAChRs in *Xenopus oocytes* are inactivated by α-bungarotoxin with high affinity, whereas other nAChRs are not. α7 nAChRs have also been pharmacologically identified by distinct types of whole cell currents elicited by nicotinic agonists in hippocampal neurons. When exposed to various nicotinic agonists whole cell recordings from cultured hippocampal neurons show, in general, type IA currents that have a very brief open time, high conductance, very high Ca$^{++}$ permeability, rapid decay, and are sensitive to blockade by MLA and α-bungarotoxin. The properties of these nicotinic currents in hippocampal neurons correspond to the currents mediated by α7 nAChRs expressed in oocytes. We are specifically interested in α7 nAChRs because of their role in regulating fast synaptic transmission in the hippocampus where it provides a specific target for the modulation of hippocampal function.

GABA$_A$ receptors that contain α5 subunits show distinct immunocytochemical, mRNA hybridization, and selective radioligand binding patterns that are specific to hippocampal structures in mammalian brain. Immunoprecipitated GABA$_A$ α subunits from the hippocampus, but not cortex or whole rat brain, show α5 immunoreactivity. Furthermore tonic inhibition of CA1 pyramidal cells in the hippocampus is mediated, in part, by GABA$_A$ α5 receptors. Genetic alteration of GABA$_A$ α5 receptors causes behavioral responses consistent with enhanced hippocampal-dependent learning and memory such as spatial learning and associative learning. A series of triazolophthalazines with selective negative allosteric modulation of GABA$_A$ α5 receptors are reported to be efficacious in the delayed matching to position test in the water maze, a hippocampal-dependent animal cognition model (Dawson et al. J. Pharmacol. Exp. Ther. 316: 1335-1345, 2006). Therefore GABA$_A$ α5 receptors may provide a suitable target for ameliorating the deficiencies in learning and memory associated with Alzheimer's disease (AD). Many ligand-gated ion channel and G-protein coupled receptor systems have been demonstrated to have diminished expression in AD brains. However, GABA$_A$ α5 receptor density and function are relatively intact in AD despite evidence for modest reductions in GABA$_A$ α5 subunit mRNA.

The simultaneous targeting of the α7 nAChR and GABA$_A$ α5 receptors with one molecule is a compelling strategy for the identification of cognition enhancing drugs in neurodegenerative diseases for several important reasons. Activation of α7 nAChRs by agonists, like nicotine, produces selective improvement of working memory. Therefore positive allosteric modulation of the α7 nAChR should also positively impact working memory. α7 nAChRs and GABA$_A$ α5 receptors are co-localized to the hippocampus and may promote neurophysiological synergism within the same locale. Negative efficacy modulation of GABA$_A$ α5 receptors improves working memory. α7 nAChRs and GABA$_A$ α5 receptors are preserved relative to the profound loss of α4β2 nAChRs as AD progresses. Moreover, patent disclosures suggest simultaneously modulating GABA and cholinergic systems with an inverse agonist and agonist, respectively, produces a " . . . surprisingly effective synergistic combination . . . " (International published application WO 1999 47142). Multifunctional allosteric modulators of α7 nAChRs and GABA$_A$ α5 receptors, such as those embodied in the current disclosure, should mitigate side effects inherent to other potential cholinergic-based therapeutic strategies for cognitive disorders because unlike direct acting α7 nAChR agonists, allosteric modulators will specifically activate the α7 nAChR only in the presence of endogenous agonist (i.e., ACh and choline). Allosteric modulators, in general, do not indiscriminately raise levels of endogenous ACh as with current clinically used acetylcholinesterase inhibitors, such as donepizal.

The allosteric modulators disclosed herein will selectively enhance the sensitivity of α7 nAChRs to the effects of local concentrations of endogenous agonists while preserving the temporal integrity of local neurotransmission. This strategy may be more advantageous than combining two drugs with each particular activity because a molecule with dual sites of action may be synergistic, thus requiring a lower dose than a molecule that targets either site of action alone reducing a) the chances for drug toxicity or b) drug-drug interactions if both receptors were targeted as a drug cocktail.

All references discussed herein are expressly incorporated by reference in their entirety.

SUMMARY OF THE INVENTION

This invention is generally directed to allosteric modulators of α5 GABA$_A$ and/or α7 nAChR, as well as to methods for their preparation and use, and to pharmaceutical compositions containing the same. More specifically, the allosteric modulators of α5 GABA$_A$ and/or α7 nAChR modulators of this invention are compounds represented by the general structure:

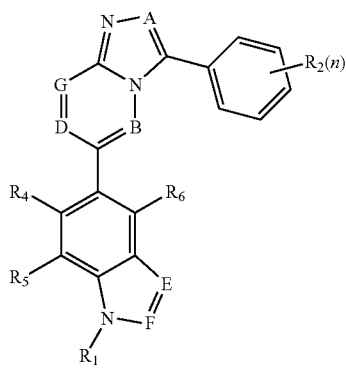

including pharmaceutically acceptable salts, esters, solvates, and prodrugs thereof, wherein R$_1$, R$_2$, R$_4$, R$_5$, R$_6$, A, B, G, D, E and F are as defined below. Further, the present invention is directed to $^3$H, $^{11}$C, $^{18}$F, $^{35}$S, $^{36}$Cl, $^{14}$C and $^{125}$I radiolabeled compounds of Formula I and their use as radioligands for their binding site on the α5 GABA$_A$ and α7 nAChR complex.

This invention also is directed to methods of treating disorders responsive to inhibition of GABA action on α5 GABA$_A$ receptors and enhancement of acetylcholine action on α7 nAChRs in a mammal by administering an effective amount of a compound of Formula I as described herein. Compounds of the present invention may be used to treat a variety of disorders, including of the central nervous system (CNS). Disorders of the CNS include but are not limited to neurodegenerative diseases, senile dementias, schizophrenia, Alzheimer's disease, learning deficit, cognition deficit, memory loss, Lewy Body dementia, attention-deficit disorder, attention deficit hyperactivity disorder, anxiety, mania, manic depression, Parkinson's disease, Huntington's disease, amyotrophic lateral sclerosis, brain inflammation and Tourette's syndrome. In addition, compounds of the present invention may be used to treat pain, inflammation, septic shock, ulcerative colitis and irritable bowel syndrome.

The present invention also is directed to pharmaceutical formulations which include a compound of the present invention. Such formulations contain a therapeutically effective amount of a compound of Formula I and one or more pharmaceutically acceptable carriers or diluents.

Additional embodiments and advantages of the invention will be set forth in part in the description that follows, and in part will be obvious from the description, or may be learned by practice of the invention. The embodiments and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF THE INVENTION

In one embodiment, there is provided a substituted bicyclic heteroarene represented by Formula I:

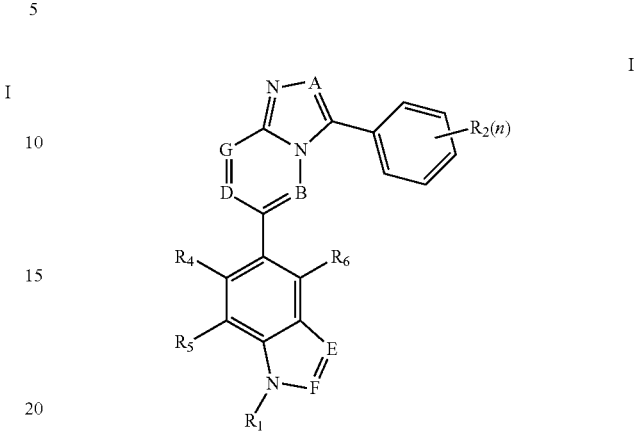

or a pharmaceutically acceptable salt, ester, solvate or prodrug thereof, wherein:
n is 1-5;
R$_1$ is selected from the group consisting of hydrogen, unsubstituted or substituted alkyl and unsubstituted or substituted cycloalkyl;
each R$_2$ is independently selected from the group consisting of hydrogen, fluoro, chloro, bromo, iodo, C$_{1-10}$alkoxy, nitro, haloC$_{1-10}$alkyl, perhaloC$_{1-10}$alkyl and unsubstituted or substituted C$_{1-10}$alkyl;
A, B, G, D, E and F are independently selected from the group consisting of CR3 or nitrogen, with the proviso that when A, B and G are carbon, D is not nitrogen;
each R$_3$ is independently selected from the group consisting of hydrogen and unsubstituted or substituted alkyl; and
R$_4$, R$_5$ and R$_6$ are independently selected from the group consisting of hydrogen and unsubstituted or substituted alkyl.

In another embodiment, there is provided substituted 1,2,4-triazolo[4,3-b]pyridazines represented by Formula II:

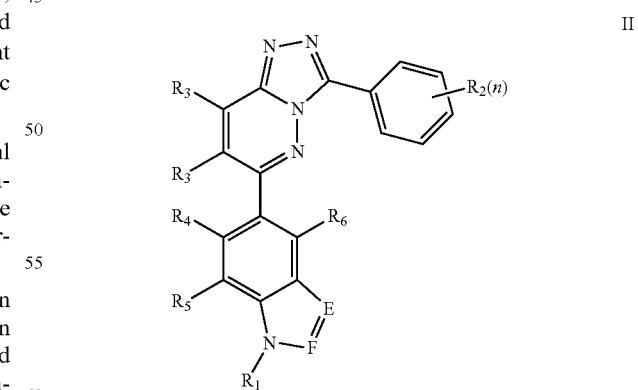

or a pharmaceutically acceptable salt, ester, solvate or prodrug thereof, wherein:
n is 1-5;
R$_1$ is selected from the group consisting of hydrogen, unsubstituted or substituted alkyl and unsubstituted or substituted cycloalkyl;

each $R_2$ is independently selected from the group consisting of hydrogen, fluoro, chloro, bromo, iodo, $C_{1-10}$alkoxy, nitro, halo$C_{1-10}$alkyl, perhalo$C_{1-10}$alkyl and unsubstituted or substituted $C_{1-10}$alkyl;

each $R_3$ is independently selected from the group consisting of hydrogen and unsubstituted or substituted alkyl;

$R_4$, $R_5$ and $R_6$ are independently selected from the group consisting of hydrogen and unsubstituted or substituted alkyl; and E and F are independently selected from the group consisting of nitrogen and $CR_3$.

In another embodiment, there is provided substituted 1,2,4-triazolo[4,3-b]pyridazines represented by Formula III:

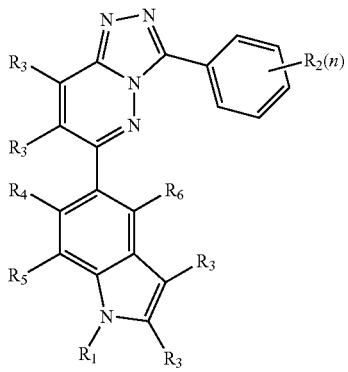

or a pharmaceutically acceptable salt, ester, solvate or prodrug thereof, wherein:

n is 1-5;

$R_1$ is selected from the group consisting of hydrogen, unsubstituted or substituted alkyl and unsubstituted or substituted cycloalkyl;

each $R_2$ is independently selected from the group consisting of hydrogen, fluoro, chloro, bromo, iodo, $C_{1-10}$alkoxy, nitro, halo$C_{1-10}$alkyl, perhalo$C_{1-10}$alkyl and unsubstituted or substituted $C_{1-10}$alkyl;

each $R_3$ is independently selected from the group consisting of hydrogen and unsubstituted or substituted alkyl; and $R_4$, $R_5$ and $R_6$ are independently selected from the group consisting of hydrogen and unsubstituted or substituted alkyl.

In another embodiment, there is provided substituted 1,2,4-triazolo[4,3-b]pyridazines represented by Formula IV:

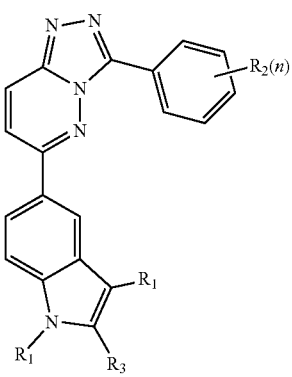

or a pharmaceutically acceptable salt, ester, solvate or prodrug thereof, wherein:

n is 1-5;

$R_1$ is selected from the group consisting of hydrogen, unsubstituted or substituted alkyl and unsubstituted or substituted cycloalkyl;

each $R_2$ is independently selected from the group consisting of hydrogen, fluoro, chloro, bromo, iodo, $C_{1-10}$alkoxy, nitro, halo$C_{1-10}$alkyl, perhalo$C_{1-10}$alkyl and unsubstituted or substituted $C_{1-10}$alkyl; and each $R_3$ is independently selected from the group consisting of hydrogen and unsubstituted or substituted alkyl.

For use in medicine, the salts of the compounds of Formulae I-IV will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, methanesulfonic acid, fumaric acid, maleic acid, succinic acid, acetic acid, benzoic acid, oxalic acid, citric acid, tartaric acid, or phosphoric acid. Furthermore, where the compounds of the invention comprises an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Standard methods for the preparation of pharmaceutically acceptable salts and their formulations are well known in the art, and are disclosed in various references, including for example, "Remington: The Science and Practice of Pharmacy", A. Gennaro, ed., 20th edition, Lippincott, Williams & Wilkins, Philadelphia, Pa.

The present invention includes within its scope prodrugs of the compounds of Formulae I-IV above. In general, such prodrugs will be functional derivatives of the compounds of Formulae I-IV that are readily convertible in vivo into the required compound of Formulae I-IV. Conventional procedures for the selection and preparation of suitable prodrug derivatives are described, for example, in Design of Prodrugs, ed. H. Bundgaard, Elsevier, 1985. Prodrugs include, but are not limited to, esters derived from alcohols, esters formed from acids, and phosphates formed from alcohols.

As used herein "solvate" refers to a complex of variable stoichiometry formed by a solute (e.g. a compound of formula (I) or a salt, ester or prodrug thereof) and a solvent. Such solvents for the purpose of the invention may not interfere with the biological activity of the solute. Examples of suitable solvents include water, methanol, ethanol and acetic acid. Generally the solvent used is a pharmaceutically acceptable solvent. Examples of suitable pharmaceutically acceptable solvents include water, ethanol and acetic acid. Generally the solvent used is water.

Where the compounds according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention. Where the compounds according to the invention possess geometrical isomers, all such isomers and mixtures thereof in any proportion are encompassed within the scope of the present invention.

"Halogen" or "halo" groups include fluorine, chlorine, bromine and iodine.

"Alkyl" means a straight or branched, saturated or unsaturated aliphatic radical with the number of carbon atoms depicted. An alkyl group may comprise a heteroatom, such as an oxygen, nitrogen or sulfur inserted within or in the chain of the alkyl group. Useful alkyl groups include straight chain and branched $C_{1-20}$alkyl groups, more preferably, $C_{1-10}$alkyl groups. The alkyl groups may be $C_{1-5}$alkyl. Typical $C_{1-10}$alkyl groups include methyl, ethyl, n-propyl, isopropyl, n-butyl, sec-butyl, iso-butyl, 1,2-dimethylpropyl, n-pentyl, 2-pentyl, 3-pentyl, n-hexyl, n-heptyl, n-octyl, n-nonyl and n-decyl groups. An alkyl group may also be represented with another group, such as an "arylalkyl" group, such as a benzyl group.

An "aryl" group may be a monocyclic, bicyclic or polycyclic ring system wherein each ring is aromatic, or when fused or connected to one or more rings to form a polycyclic ring system. An aryl ring may also be fused with a non-aromatic ring. An aryl ring may also contain a heteroatom to form a heteroaryl ring. Useful aryl groups are $C_{6-14}$aryl, especially $C_{6-10}$aryl. Typical $C_{6-14}$aryl groups include phenyl, naphthyl, anthracenyl, indenyl and biphenyl groups.

An "arylalkyl" or "aralkyl" group includes any of the above-mentioned $C_{1-20}$alkyl groups substituted with any of the above-mentioned $C_{6-10}$aryl groups. Similarly, a substituted $C_{1-10}$alkyl may also represent an arylalkyl or aralkyl group (or heteroarylalkyl, etc.) when the $C_{1-10}$alkyl group is substituted with an aryl group. Useful arylalkyl groups include any of the above-mentioned $C_{1-20}$alkyl groups substituted with any of the above-mentioned $C_{6-10}$aryl groups. Useful arylalkyl groups include benzyl and phenethyl.

"Cycloalkyl" groups include cyclopropyl, cyclobutyl, cyclopentyl, cyclohexyl, cycloheptyl and cyclooctyl groups.

"Cycloalkylalkyl" groups include any of the above-mentioned $C_{1-20}$alkyl groups substituted with any of the previously mentioned cycloalkyl groups. Examples of useful cycloalkylalkyl groups include cyclohexylmethyl and cyclopropylmethyl groups.

"Haloalkyl" groups are $C_{1-20}$alkyl groups substituted with one or more fluorine, chlorine, bromine or iodine atoms, including for example, fluoromethyl, difluoromethyl, trifluoromethyl and 1,1-difluoroethyl groups. The term haloalkyl also includes perhaloalkyl groups, which include, for example, trifluoromethyl and pentafluoroethyl groups.

"Hydroxyalkyl" groups include $C_{1-20}$alkyl groups substituted by one or more hydroxyl and include hydroxymethyl, 1- and 2-hydroxyethyl and 1-hydroxypropyl groups.

"Alkoxy" groups are groups attached through an oxygen which is substituted by an alkyl group defined above.

"Alkylthio" groups are groups attached through a sulfur which is substituted by an alkyl group defined above and includes, for example, methyl- and ethylthio groups.

An "amino" group is $-NH_2$. An alkylamino and dialkylamino group, for example, include the groups $-NHR'$ and $-NR'R''$, wherein each R' and R'' are independently substituted or unsubstituted alkyl groups defined above. Example of such groups include $-NHMe$, $-NHEt$, $-NHcyclohexyl$, $-NHCH2phenyl$, $-N(Me)_2$, and the like. Useful dialkylaminoalkyl groups include any of the above-mentioned $C_{1-10}$alkyl groups, each substituted or unsubstituted. Also, a substituted amino group may include for example, $-NHMe$, $-NHEt$, $-NHcyclohexyl$, $-N(Me)_2$ and the like.

"Alkylthiol" groups are any of the above-defined alkyl groups substituted by a $-SH$ group.

A "carboxy" group is $-COOH$.

The term "heterocyclic" is used herein to mean saturated or partially unsaturated 3-7 membered monocyclic, or 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or nitrogen if the resulting compound is stable. Examples include, but are not limited to pyrrolidine, piperidine, piperazine, morpholine, 1,2,3,4-tetrahydroquinoline, and the like.

The term "heteroaryl" is used herein to mean wholly unsaturated 5 and 6 membered monocyclic, or 9 and 10 membered bicyclic ring system, which consists of carbon atoms and from one to four heteroatoms independently selected from the group consisting of O, N, and S, wherein the nitrogen and sulfur heteroatoms can be optionally oxidized, for example, to form $-N(O)-$, $-SO-$, $SO_2-$, the nitrogen can be optionally quaternized; and including any bicyclic group in which any of the above-defined heterocyclic rings is fused to a benzene ring, and wherein the heteroaryl ring can be substituted on carbon or nitrogen if the resulting compound is stable. Examples include, but are not limited to pyridine, pyrimidine, pyradizine, tetrazole, imidazole, isoxazole, oxazole, 1,2,4-oxadiazole, 1,2,3-oxadiazole, quinoline, and the like.

"Isomers" mean any compound with an identical molecular formula but having a difference in the nature or sequence of bonding or arrangement of the atoms in space. Examples of such isomers include, for example, E and Z isomers of double bonds, enantiomers, and diastereomers.

"Substituted or unsubstituted" means that a group may consist of only hydrogen substituents (unsubstituted) or may further comprise one or more non-hydrogen substituents (substituted) that are not otherwise specified. For example, tert-butyl group may be an example of a propyl group that is substituted by a methyl group. Examples of substituents include, but are not limited to, $C_{1-10}$alkyl, $C_{2-10}$alkylene, amide, amino, alkylamino, dialkylamino, aryl, carbamoyl, carbonyl group, cycloalkyl, ester, halo, heteroaryl, oxo, hydroxy or nitro groups, each of which may also be substituted or unsubstituted as valency permits. Optional substituents on $R_1$ to $R_6$ include any one of halo, halo($C_{1-20}$)alkyl, aryl, aryloxy, heteroaryl, heteroaryloxy, cycloalkyl, cycloalkyloxy, $C_{1-20}$alkyl, aryl($C_{1-20}$)alkyl, cycloalkyl($C_{1-20}$)alkyl, hydroxy($C_{1-20}$)alkyl, amino($C_{1-20}$)alkyl, alkoxy ($C_{1-20}$)alkyl, amino, alkylamino, dialkylamino, hydroxy, cyano, nitro, thiol, $C_{1-20}$alkoxy and $C_{1-20}$alkylthiol groups mentioned above. Preferred optional substituents include: halo, halo($C_{1-6}$)alkyl, amino($C_{1-6}$)alkyl, alkoxy, hydroxyl, amino, alkylamino and dialkylamino.

As used herein "allosteric modulator" of α5 GABAA and/or α7 nAChR refers to a compound that that binds allosterically to α5 GABAA and/or α7 nAChR, thereby increasing (positive allosteric modulator) or decreasing (negative allosteric modulator) the agonist-evoked response.

As used herein a "disorder amenable to modulation of α5 GABAA and α7 nAChR" refers to a disorder associated with α5 GABAA and α7 nAChR dysfunction and/or a disorder in which α5 GABAA and α7 nAChR receptors are involved. Such disorders include, but are not limited to neurodegenerative diseases, senile dementias, schizophrenia, Alzheimer's disease, learning deficits, cognition deficits memory loss, Lewy Body dementia, attention-deficit disorder, attention deficit hyperactivity disorder, anxiety, mania, manic depression, Parkinson's disease, Huntington's disease, amyotrophic lateral sclerosis, brain inflammation, Tourette's syndrome, pain, inflammation, septic shock, ulcerative colitis and irritable bowel syndrome.

As used herein "a cognitive disorder related to learning or memory" refers to a mental disorder that affects cognitive functions, such as memory, learning, perception, problem-solving, conceptualization, language, reading comprehension, linguistic comprehension, verbal comprehension, math comprehension, visual comprehension and attention. Cognitive disorders related to learning or memory include, but are not limited to, mild cognitive impairment, age related cognitive decline, senile dementia and Alzheimer's disease.

The preparation of the compounds of the present invention may be performed using the standard methods know in the art of organic synthesis. Reactions using compounds having functional groups may be performed on compounds with functional groups that may be protected. A "protected" compound or derivatives means derivatives of a compound where one or more reactive site or sites or functional groups are blocked with protecting groups. Protected derivatives are useful in the preparation of the compounds of the present invention or in themselves; the protected derivatives may be the biologically active agent. An example of a comprehensive text listing suitable protecting groups may be found in T. W. Greene, *Protecting Groups in Organic Synthesis,* 3rd edition, John Wiley & Sons, Inc. 1999.

As mentioned above, the allosteric modulators of this invention have utility over a wide range of therapeutic applications, and may be used to treat a variety of CNS related conditions in humans, as well as mammals in general. For example, such conditions include neurodegenerative diseases, senile dementias, schizophrenia, Alzheimer's disease, learning deficit, cognition deficit, memory loss, Lewy Body dementia, attention-deficit disorder, attention deficit hyperactivity disorder, anxiety, mania, manic depression, Parkinson's disease, Huntington's disease, amyotrophic lateral sclerosis, brain inflammation and Tourette's syndrome.

In addition, the compounds of this invention may be useful in combination with compounds which are direct modulators of α7 nAChR and/or α5 GABAA receptors for the treatment of CNS related conditions.

In another embodiment of the invention, pharmaceutical compositions containing one or more compounds of the invention are disclosed. For the purposes of administration, the compounds of the present invention may be formulated as pharmaceutical compositions. Pharmaceutical compositions of the present invention comprise a compound of the present invention and a pharmaceutically acceptable carrier and/or diluent. The compound of the invention is present in the composition in an amount that is effective to treat a particular disorder, preferably with acceptable toxicity to the patient. Typically, the pharmaceutical compositions of the present invention may include a compound of the invention in an amount from 0.1 mg to 250 mg per dosage depending upon the route of administration, and more typically from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a compound of the invention, diluents, dispersing and surface active agents, binders, and lubricants. One skilled in this art may further formulate a compound of the present invention in an appropriate manner, and in accordance with accepted practices, such as those disclosed in Remington's Pharmaceutical Sciences, Gennaro, Ed., Mack Publishing Co., Easton, Pa. 1990.

In another embodiment, the present invention provides a method for treating CNS related conditions as discussed above. Such methods include administering of a compound of the present invention to a warm-blooded animal in an amount sufficient to treat the condition. In this context, "treat" includes prophylactic administration. Such methods include systemic administration of a compound of this invention, preferably in the form of a pharmaceutical composition as discussed above. As used herein, systemic administration includes oral and parenteral methods of administration. For oral administration, suitable pharmaceutical compositions of this invention include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to a compound of the invention, buffers, antioxidants, bacteriostats, and other additives commonly employed in such solutions.

Compounds of Formula IV were prepared as shown in Scheme 1 starting with commercially available 3,6-dichloropyridazine. Reaction with a benzoic hydrazide gave the intermediate that was cyclized to the 1,2,4-triazolo[4,3-b]pyridazine using Et₃NHCl in xylene. Boronic acid coupling of the chloride then gave the desired products. Alternatively, the boronic acid coupling can be accomplished first, followed by reaction with the benzoic hydrazide. The benzoic hydrazides were prepared from the corresponding benzoic acids as shown in Scheme 2.

Scheme 1

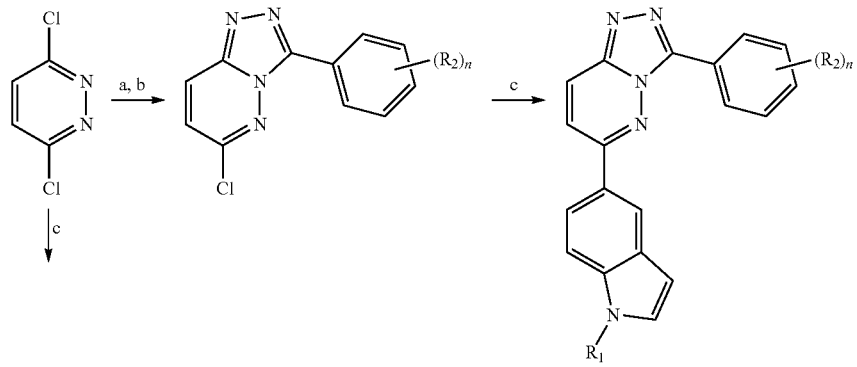

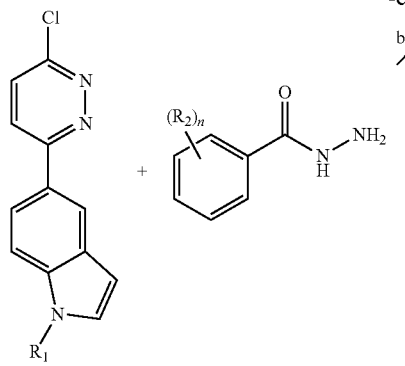

Reagents/conditions: a) ArCONHNH$_2$ b) Et$_3$NHCl/toluene/DMF. c) HeteroarylB(OH)$_2$/Na$_2$CO$_3$/Ph(PPh$_3$)$_4$/H$_2$O/EtOH/toluene.

Scheme 2

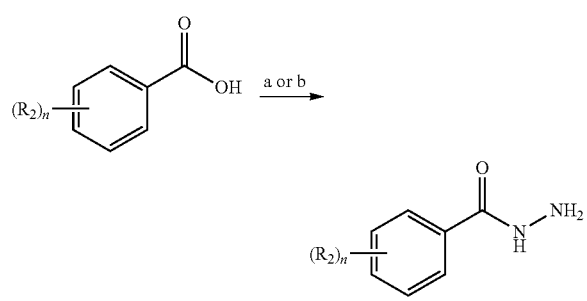

Reagents/conditions: a) i. SOCl$_2$/CH$_2$Cl$_2$ ii. Hydrazine hydrate. b) i. ROH/Acid ii. Hydrazine hydrate Oocyte Electrophysiology:

Individual compounds were tested for modulation of submaximal nicotine-evoked currents at α7 nAChRs using oocytes expressing human receptors. For each oocyte, the maximal nicotine-evoked currents were determined in response to 3 mM nicotine. All other currents were scaled to this value. The concentration of nicotine was adjusted to evoke a fractional current of approximately 0.05 (5% of max, or "EC$_5$"), and this concentration of nicotine was used to generate EC$_5$ control currents. Increasing concentrations of test compounds were applied to oocytes alone (pretreatment) and then in combination with the EC$_5$ concentration of nicotine (co-application). This protocol allowed measurement of both direct effects of test compounds on α7 nAChRs, and modulatory effects of compounds on nicotine-evoked responses. mRNA was prepared and stored using conventional techniques from cDNA clones encoding the human nicotinic receptor subunits. Preparation, micro-injection and maintenance of oocytes were performed as reported in detail previously (Whittemore et al., Mol. Pharmacol. 50: 1364-1375, 1996). Individual oocytes were injected with 5-50 ng of each subunit mRNA. Following injections, oocytes were maintained at 16-17° C. in Barth's medium. Two-electrode voltage clamp recordings were made 3-14 days following mRNA injections at a holding voltage of −70 mV unless specified. The nicotinic recordings were done in Ca$^{++}$-free Ringer solution (mM: NaCl, 115; KCl, 2; BaCl$_2$, 1.8; HEPES, 5; pH 7.4) to limit Ca$^{++}$-activated chloride and muscarinic currents. Compounds of the present invention were found to have maximum positive modulation at α7 nAChRs of greater than 100% at 10 μM concentration. Certain compounds of the invention were found to have maximum positive modulation at α7 nAChRs of greater than 500% and, in certain instances, greater than 1000% at 10 μM concentration.

Compounds were tested using similar methods for inhibition of submaximal GABA-induced currents at α5 GABA$_A$ receptors. The EC$_{20}$ GABA concentration was used as the baseline response. Drug and wash solutions were applied using a microcapillary "linear array" (Hawkinson et al., Mol. Pharmacol. 49: 897-906, 1996) in order to allow rapid application of agonists. Currents were recorded on a chart recorder and/or PC-based computer for subsequent analysis. Test compounds were made up in DMSO over a concentration range of 0.001-10 mM and diluted 1000-3000-fold into the appropriate saline just prior to testing (final [DMSO]≤0.1%). The concentration-dependence of modulation was analyzed using GraphPad "Prism" curve-fitting software. Compounds of the present invention were found to have maximum negative modulation of α5 GABA$_A$ receptors of from 5% to 50% at 10 μM concentration.

Positive allosteric modulators of α7 nAChR can also be assayed by imaging of calcium flux through α7 nAChR transiently expressed in a cell line, including HEK-293 and cell cultured neurons (see for example WO 2006/071184). Activation of native α7 nAChRs, by electrophysiological recordings in rat hippocampal slices can also be used to measure the effect of allosteric modulators. The effect can be observed on the activation of α7 nAChR mediated currents in hippocampal CA1 stratum radiatum interneurons by the application of ACh in the presence of an allosteric modulator.

Behavioral: Cognition Measurements.

Mice were placed facing away from the door in the lit compartment of a 2 compartment activity chamber (Model E63-12, Coulbourn Instruments, Allentown, Pa.) with a guillotine door separating the lit from dark compartments. After 5 seconds, the guillotine door was raised and the entrance latency to the dark compartment (step-through latency) was recorded when the animal places all four paws in the dark compartment. After the animal spontaneously entered the dark compartment, the guillotine door was lowered and a 50 Hz square wave, 0.25 mA constant current shock was applied for 1.0 s. After 20-24 hours, the latency to enter the dark chamber was measured again. Various doses of test drug were administered 10 m before or immediately after the acquisition trial to measure drug effects on acquisition and consolidation respectively. The difference between test latency and acquisition latency was recorded and a significant (ANOVA, post-hoc Newman Keuls) increase in latency over controls suggests a positive effect on memory. The ability to restore disruption of acquisition and consolidation by the muscarinic antagonist scopolamine was also measured (Sarter et al., Psychopharmacologia 107: 144-159, 1992). Compounds of the present invention were found to have activity in the radial arm maze paradigm at <10 mg/kg ip, at <1 mg/kg ip in other instances and in certain instances at <0.1 mg/kg ip. Sedation. Rotarod performance was measured as previously described to assess possible CNS depressant effects (Johnstone et al., Nat. Med. 10: 31-32, 2004). Compounds tested did not disrupt rotarod performance.

The compounds of the present invention exemplified below were found to have maximum positive modulation at α7 nAChRs of greater than 100% and maximum negative modulation of α5 $GABA_A$ receptors of from 10% to 50% at 10 µM concentration.

Example 1

3-(2,5-Difluorophenyl)-6-(1H-indol-5-yl)-1,2,4-triazolo[4,3-b]pyridazine

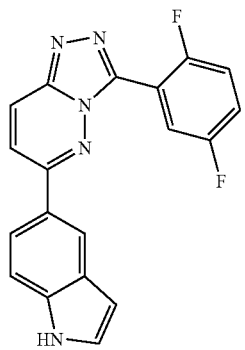 [SMILES: Fc1ccc(F)c(-c2nnc3ccc(-c4ccc5[nH]ccc5c4)nn23)c1]

a. 5-(6-Chloro-3-pyridazinyl)-1H-indole

To a solution of $Na_2CO_3$ (0.70 g, 6.6 mmol) in $H_2O$ (5 mL) was added indole-5-boronic acid (1.0 g, 6.2 mmol) and EtOH (25 mL). After stirring at rt for 30 min, 3,6-dichloropyridazine (935 mg, 6.30 mmol), toluene (50 mL) and $Pd(PPh_3)_4$ (0.30 g) were added. The mixture was stirred at 90° C. for 30 h and then evaporated in vacuo. The residue was treated with $CH_2Cl_2$ (100 mL), washed with brine, dried ($Na_2SO_4$), filtered and concentrated. The residue was purified by flash chromatography, eluting with ($CH_2Cl_2$-MeOH=100:5) to give 0.35 g (37% yield) of the product as a yellow solid. $^1$H NMR (DMSO-$d_6$) δ 6.52 (1H, s), 7.40 (1H, s), 7.50 (1H, d, 6.3 Hz), 7.86-7.90 (2H, m), 8.27 (1H, d, 6.9 Hz), 8.32 (1H, s), 11.32 (1H, s). MS m/e 230 (M+H$^+$); Calculated MW: 229 for $C_{12}H_8ClN_5$.

b. 2,5-Difluorobenzoic hydrazide

To a solution of 2,5-difluorobenzoic acid (5.0 g, 31.6 mmol) in $CH_2Cl_2$ (60 mL) was added $SOCl_2$ (23 mL) slowly at rt. The mixture was refluxed for 3 h, allowed to cool and concentrated in vacuo. The residue was treated with toluene and concentrated in vacuo. A solution of the crude acid chloride in $CH_2Cl_2$ (100 mL) was treated with anhydrous hydrazine (5.0 g) and heated at reflux for 4 h. Once at rt, the reaction was washed with brine, dried over $Na_2SO_4$, filtered and evaporated. The resulting solid was recrystallized from MeOH (20 mL). The colorless crystals were collected by filtration and dried to give 1.99 g (56% yield) of the hydrazide. $^1$H NMR (DMSO-$d_6$) δ 4.52 (2H, s), 7.29-7.33 (3H, m), 9.53 (1H, s). MS m/e 173 (M+H$^+$); Calculated MW: 172 for $C_7H_6F_2N_2O$.

c. 3-(2,5-Difluorophenyl)-6-(1H-indol-5-yl)-1,2,4-triazolo[4,3-b]pyridazine

A mixture of 5-(6-chloro-3-pyridazinyl)-1H-indole (0.85 g, 3.7 mmol), 2,5-difluorobenzoic hydrazide (0.64 g, 3.7 mmol) and $Et_3N$ HCl (0.5 g, 3.6 mmol) in toluene (20 mL) and DMF (2 mL) was stirred at 150° C. for 3 days and then evaporated to dryness. The residue was treated with $CH_2Cl_2$ (100 mL), washed with brine (3×100 mL), dried ($Na_2SO_4$), filtered and evaporated. The residue was purified by flash chromatography, eluting with $CH_2Cl_2$-MeOH (100:5), to give 400 mg (31% yield) of the product as a yellow solid. $^1$HNMR (DMSO-$d_6$) δ 6.53 (1H, s), 7.41 (1H, s), 7.50-7.58 (3H, m), 7.76 (1H, d, J=6.3 Hz), 7.85-7.90 (1H, m), 8.08 (1H, d, J=7.2 Hz), 8.28 (1H, s), 8.46 (1H, d J=7.2 Hz), 11.39 (1H, s). MS m/e 348 (M+H$^+$); Calculated MW: 347 for $C_{19}H_{11}F_2N_5$.

THE following compounds were prepared by using the method described above for the synthesis of 3-(2,5-difluorophenyl)-6-(1H-indol-5-yl)-1,2,4-triazolo[4,3-b]pyridazine:

3-(2-Chlorophenyl)-6-(1H-indol-5-yl)-1,2,4-triazolo[4,3-b] pyridazine, MS 340 (M+H$^+$);

3-phenyl-6-(1H-indol-5-yl)-1,2,4-triazolo[4,3-b]pyridazine, MS 312 (M+H$^+$); and 3-(3,4-difluorophenyl)-6-(1H-indol-5-yl)-1,2,4-triazolo[4, 3-b]pyridazine MS 348 (M+H$^+$).

Example 2

3-(2,5-Difluorophenyl)-6-(1-ethyl-1H-indol-5-yl)-1,2,4-triazolo[4,3-b]pyridazine

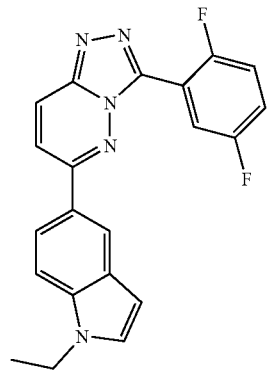 [SMILES: CCn1ccc2cc(-c3ccc4nnc(-c5cc(F)ccc5F)n4n3)ccc21]

A mixture of 3-(2,5-difluorophenyl)-6-(1H-indol-5-yl)-1, 2,4-triazolo[4,3-b]pyridazine (0.37 g, 1.0 mmol) and powdered NaOH (60 mg, 1.5 mmol) in DMF (15 mL) was stirred at rt for 30 min and iodoethane (300 mg, 1.9 mmol) was added. The mixture was stirred at rt for 16 h and evaporated to dryness. The residue was treated with $CH_2Cl_2$ (60 mL), washed with brine (3×100 mL), dried ($Na_2SO_4$), filtered, and evaporated. The residue was purified by flash chromatography, eluting with $CH_2Cl_2$-MeOH (100:5), to give 290 mg (80% yield) of the product as an off-white solid. $^1$H NMR (DMSO-$d_6$) δ 1.33 (3H, t, J=5.4 Hz), 4.21 (2H, q, J=5.4 Hz), 6.55 (1H, d, J=2.1 Hz), 7.47 (1H, d, J=2.1 Hz), 7.54-7.59 (2H, m), 7.63 (1H, d, J=6.3 (1H, d, J=6.3 Hz), 7.81 (1H, d J=6.9 Hz), 7.87-7.91 (1H, m), 8.09 (1H, d, J=7.2 Hz), 8.28 (1H, s), 8.47 (1H, d J=7.2 Hz). MS m/e 376 (M+H$^+$); Calculated MW: 375 for $C_{21}H_{15}F_2N_5$.

The following compounds were prepared by using the method described above for the synthesis of 3-(2,5-difluorophenyl)-6-(1-ethyl-1H-indol-5-yl)-1,2,4-triazolo[4,3-b]pyridazine:

3-(2,5-Difluorophenyl)-6-(1-methyl-1H-indol-5-yl)-1,2,4-triazolo[4,3-b]-pyridazine, MS 362 (M+H$^+$);

3-(2,5-difluorophenyl)-6-(1-propyl-1H-indol-5-yl)-1,2,4-triazolo[4,3-b]-pyridazine, MS 390 (M+H$^+$);

3-(3,4-difluorophenyl)-6-(1-propyl-1H-indol-5-yl)-1,2,4-triazolo[4,3-b]-pyridazine, MS 390 (M+H$^+$); and 3-phenyl-6-(1-ethyl-1H-indol-5-yl)-1,2,4-triazolo[4,3-b]pyridazine, MS 340 (M+H$^+$).

What is claimed is:

1. A compound of Formula I:

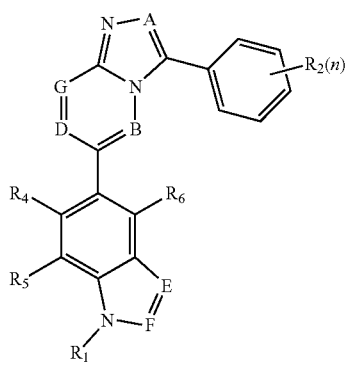

or a pharmaceutically acceptable salt thereof, wherein:
n is 1-5;
$R_1$ is selected from the group consisting of hydrogen, unsubstituted or substituted alkyl and unsubstituted or substituted cycloalkyl;
each $R_2$ is independently selected from the group consisting of hydrogen, fluoro, chloro, bromo, iodo, $C_{1-10}$alkoxy, nitro, halo$C_{1-10}$alkyl, perhalo$C_{1-10}$alkyl and unsubstituted or substituted $C_{1-10}$alkyl;
A, E and F are independently selected from the group consisting $CR_3$ and nitrogen;
B is nitrogen;
G and D are each carbon;
each $R_3$ is independently selected from the group consisting of hydrogen and unsubstituted or substituted alkyl; and
$R_4$, $R_5$ and $R_6$ are independently selected from the group consisting of hydrogen and unsubstituted or substituted alkyl.

2. The compound of claim 1, which is represented by Formula II:

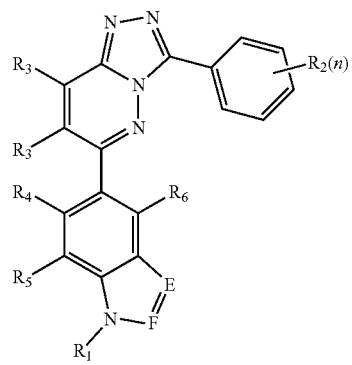

wherein:
n is 1-5;
$R_1$ is selected from the group consisting of hydrogen, unsubstituted or substituted alkyl and unsubstituted or substituted cycloalkyl;
each $R_2$ is independently selected from the group consisting of hydrogen, fluoro, chloro, bromo, iodo, $C_{1-10}$alkoxy, nitro, halo$C_{1-10}$alkyl, perhalo$C_{1-10}$alkyl and unsubstituted or substituted $C_{1-10}$alkyl;
each $R_3$ is independently selected from the group consisting of hydrogen and unsubstituted or substituted alkyl;
$R_4$, $R_5$ and $R_6$ are independently selected from the group consisting of hydrogen and unsubstituted or substituted alkyl; and
E and F are independently selected from the group consisting of nitrogen and $CR_3$.

3. The compound of claim 2, which is represented by Formula III:

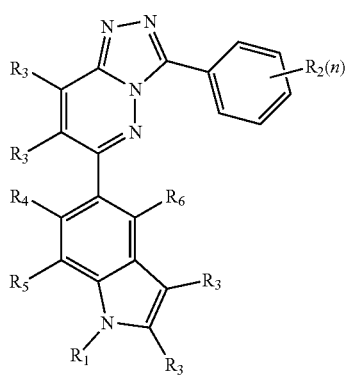

wherein:
n is 1-5;
$R_1$ is selected from the group consisting of hydrogen, unsubstituted or substituted alkyl and unsubstituted or substituted cycloalkyl;
each $R_2$ is independently selected from the group consisting of hydrogen, fluoro, chloro, bromo, iodo, $C_{1-10}$alkoxy, nitro, halo$C_{1-10}$alkyl, perhalo$C_{1-10}$alkyl and unsubstituted or substituted $C_{1-10}$alkyl;
each $R_3$ is independently selected from the group consisting of hydrogen and unsubstituted or substituted alkyl; and
$R_4$, $R_5$ and $R_6$ are independently selected from the group consisting of hydrogen and unsubstituted or substituted alkyl.

4. The compound of claim 3, which is represented by Formula IV:

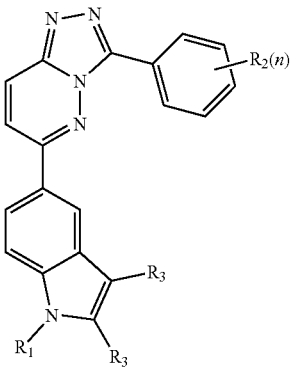

IV wherein:

n is 1-5;

$R_1$ is selected from the group consisting of hydrogen, unsubstituted or substituted alkyl and unsubstituted or substituted cycloalkyl;

each $R_2$ is independently selected from the group consisting of hydrogen, fluoro, chloro, bromo, iodo, $C_{1-10}$alkoxy, nitro, halo$C_{1-10}$alkyl, perhalo$C_{1-10}$alkyl and unsubstituted or substituted $C_{1-10}$alkyl; and each $R_3$ is independently selected from the group consisting of hydrogen, unsubstituted or substituted alkyl and unsubstituted or substituted alkyl.

5. A pharmaceutical composition comprising a compound according to claim 1, and a pharmaceutically acceptable carrier or diluent.

* * * * *